United States Patent
Nagamine

(10) Patent No.: US 8,742,348 B2
(45) Date of Patent: Jun. 3, 2014

(54) MUON MONITORING SYSTEM FOR CHARGED PARTICLE RADIATION THERAPY

(75) Inventor: Kanetada Nagamine, Kashiwa (JP)

(73) Assignee: Inter-University Research Institute Corp. High Energy Accelerator Research Organization, Tsukuba-shi (JP)

( * ) Notice: Subject to any disclaimer, the term of this patent is extended or adjusted under 35 U.S.C. 154(b) by 0 days.

(21) Appl. No.: 13/581,969

(22) PCT Filed: Mar. 2, 2011

(86) PCT No.: PCT/JP2011/054787
§ 371 (c)(1),
(2), (4) Date: Oct. 11, 2012

(87) PCT Pub. No.: WO2011/108601
PCT Pub. Date: Sep. 9, 2011

(65) Prior Publication Data
US 2013/0046127 A1    Feb. 21, 2013

(30) Foreign Application Priority Data
Mar. 2, 2010 (JP) ................................. 2010-045774

(51) Int. Cl.
*G01T 1/00* (2006.01)
*A61N 5/00* (2006.01)
*A61N 5/10* (2006.01)
*G01T 1/29* (2006.01)
*G01N 23/00* (2006.01)

(52) U.S. Cl.
CPC ............... *A61N 5/10* (2013.01); *A61N 5/1048* (2013.01); *A61N 2005/1052* (2013.01); *G01T 1/29* (2013.01); *G01N 23/00* (2013.01)
USPC ................... 250/336.1; 250/358.1; 250/267; 600/1; 600/2

(58) Field of Classification Search
CPC ................ A61N 5/10; A61N 5/1048; A61N 2005/1052; G01T 1/29; G01N 23/00
USPC ............. 250/267, 307, 336.1, 358.1; 600/1, 2
See application file for complete search history.

(56) References Cited

U.S. PATENT DOCUMENTS 5,937,202 A * 8/1999 Crosetto ........................ 712/19
6,705,984 B1 * 3/2004 Angha .............................. 600/2
(Continued)

FOREIGN PATENT DOCUMENTS

JP  2008-014816  1/2008
JP  2008-022994  2/2008
(Continued)

*Primary Examiner* — Duc M Nguyen
(74) *Attorney, Agent, or Firm* — Manabu Kanesaka

(57) ABSTRACT

A muon monitoring system for particle radiation therapy includes: a shield for a selective passing, by eliminating particles and radiation produced due to the high energy particles and radiation pulses, of the delay positrons emitted due to decay of muons stopped at a position corresponding to the Bragg peak position; a positron detector for detecting positrons from a designated direction and detecting the delay positrons passed through the shield opening by each of positron detecting plates for providing information of positron produced positions and time of delay simultaneous signals; and a control/analysis apparatus generating a delay signal at a timing delayed by a predetermined time period from a completion of irradiation of the high energy particle radiation pulses, and performing a process to generate μSR signals segmented for each positron generating position by analyzing detected results obtained by operating the positron detector for a predetermined number of times.

4 Claims, 10 Drawing Sheets

(56) References Cited

U.S. PATENT DOCUMENTS

| | | | | |
|---|---|---|---|---|
| 7,863,571 B2* | 1/2011 | Beken | .................. | 250/358.1 |
| 8,109,865 B2* | 2/2012 | Jackson | .................. | 600/1 |
| 8,384,017 B2* | 2/2013 | Botto | .................. | 250/266 |
| 8,426,814 B2* | 4/2013 | Kraft | .................. | 250/336.1 |
| 2011/0001046 A1* | 1/2011 | Nagamine | .................. | 250/307 |
| 2011/0231147 A1* | 9/2011 | Takayanagi et al. | .................. | 702/150 |

FOREIGN PATENT DOCUMENTS

| | | |
|---|---|---|
| JP | 2008-173299 | 7/2008 |
| JP | 2009-261634 | 12/2009 |
| WO | 2009-107575 | 9/2009 |

* cited by examiner

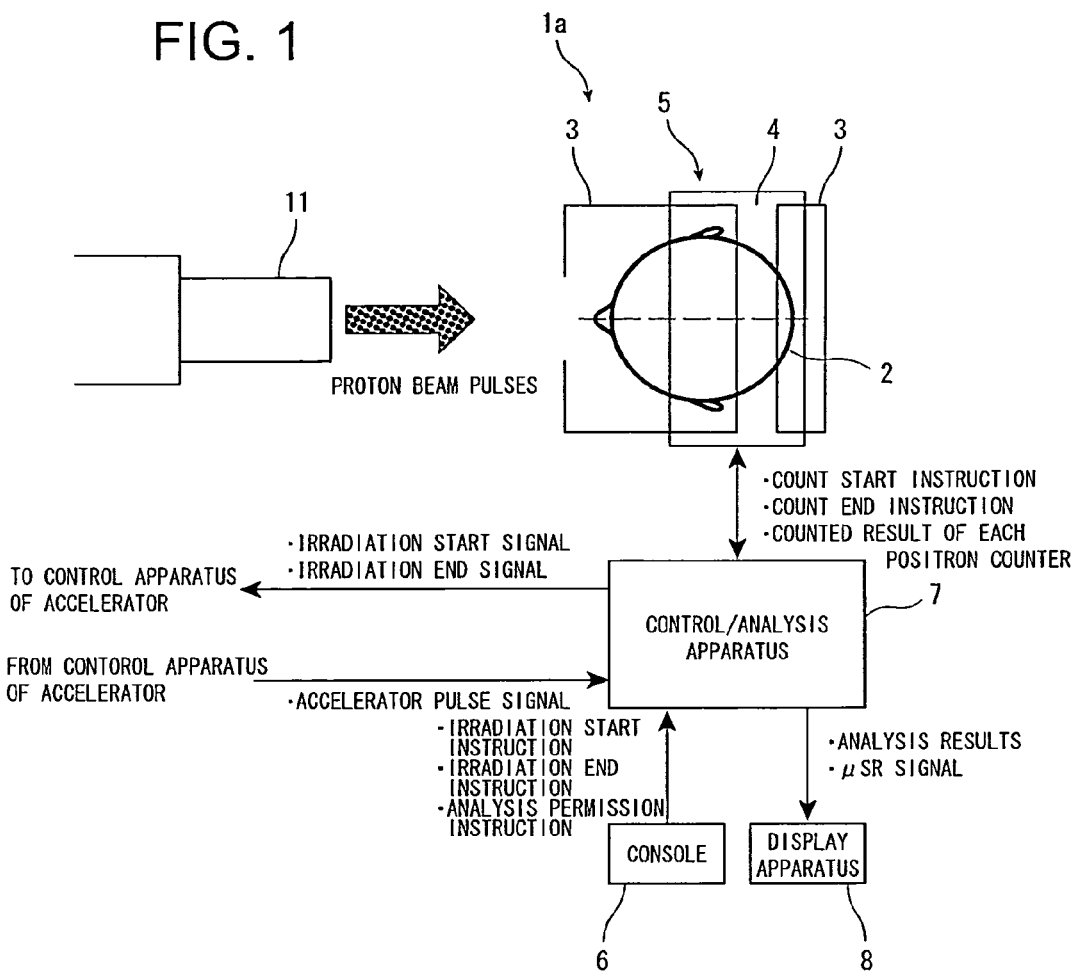
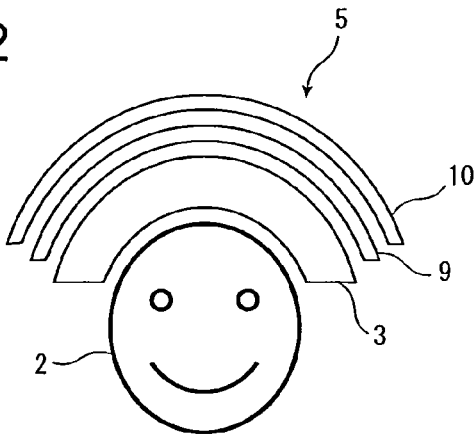

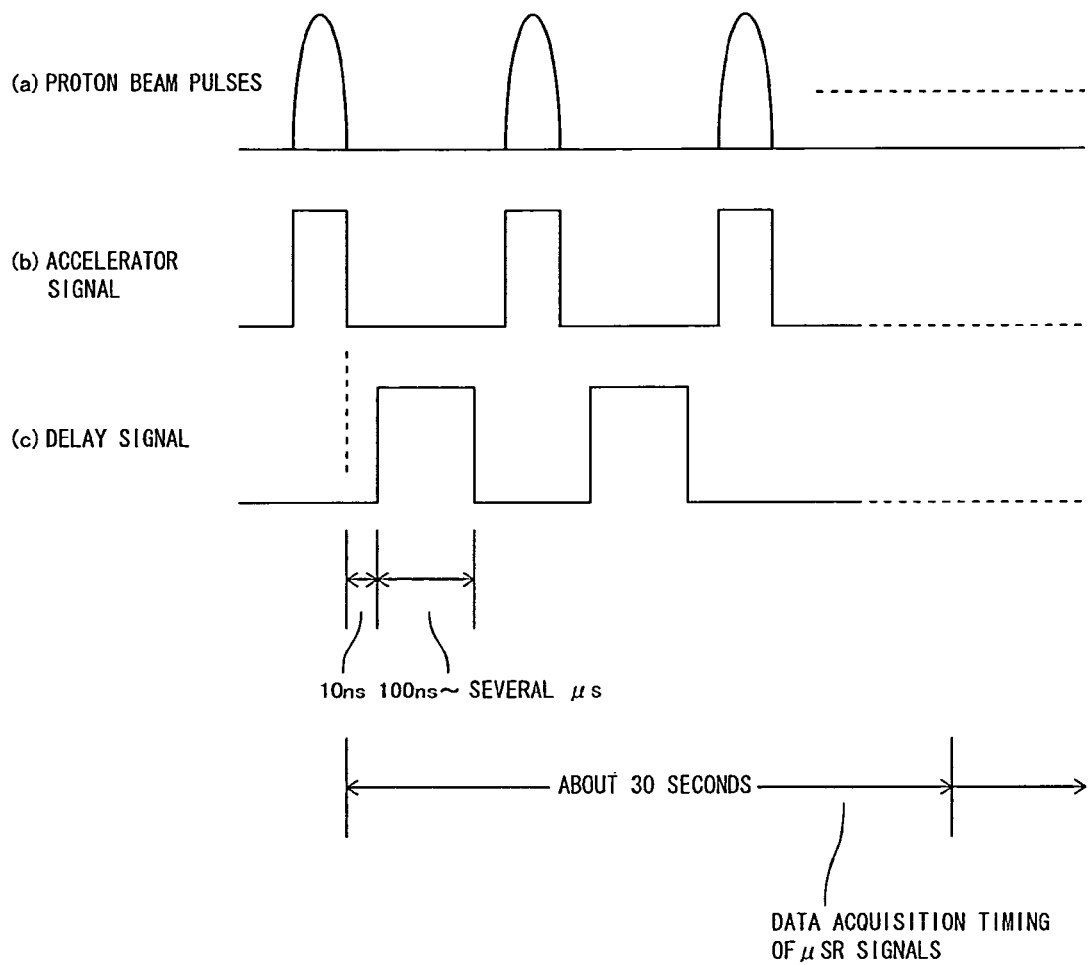

A: 5cm
B: 20cm
C: 30cm

MUON MONITORING SYSTEM FOR CHARGED PARTICLE RADIATION THERAPY

TECHNICAL FIELD

The present invention relates to a muon monitoring system for charged particle radiation therapy utilizing proton beams or the like used in radiology or the like, and in particular, relates to a muon monitoring system, for radiation therapy, enabling direct detection of a radiological effect at a Bragg peak.

BACKGROUND ART

At present, a radiation therapy utilizing high energy charged particle radiation, such as radiation of protons, heavy ions or the like, is put in practical use as one of therapy for cancer.

Moreover, using a monitoring apparatus of a PET system, a monitoring apparatus of a gamma ray system or the like, the method of the In-situ monitoring the radiation therapy effect exactly on a present spot is also proposed.

For example, in the monitoring apparatus of the In-situ PET system, using the positron generating nuclei which arise by nuclear reactions of particle radiation, a PET observation is performed to conduct an ultimate analysis of the positions of passing protons.

Moreover, in the monitoring apparatus of the In-situ Gamma system, an ultimate analysis is conducted by catching characteristic gamma rays produced from nuclear reactions of proton beams.

PRIOR ART DOCUMENTS

Patent Documents

PATENT DOCUMENTS 1: Japanese Laid Open Patent Publication (Kokai) No. 2009-261634
PATENT DOCUMENTS 2: Japanese Laid Open Patent Publication (Kokai) No. 2008-173299

SUMMARY OF THE INVENTION

Problems to be Solved by the Invention

However, in these conventionally proposed monitoring apparatus, there are following problems.

First, by the PET method, since the observation had to be conducted after stopping the beams and waiting for nuclear decay, there was a problem in that it took time too much before obtaining the result of the observation. Moreover, since a nuclear reaction occurs above a MeV (million electron volt) level, there was a problem in that a position will shift by more than 10 cm from the Bragg peak which appears just before a proton or the like stops.

Moreover, since the Gamma method can handle short life nuclei, observing time is shorter than that of the PET method. However, there was a problem in that the position of the nucleus observed is largely shifted from the Bragg peak position as in the same way as in the PET method.

Furthermore, in these two techniques, since element analysis is a main purpose, there was a problem in that physical chemistry phenomena of radiological effects in living thing could not be observed.

For this reason, a development of a methodology has been strongly desired, in which, at the Bragg peak position where the radiological effect of charged particle radiation is to be the maximum, a certain "noninvasive in-situ observation" can be performed so that the radiation therapy effect can be monitored exactly so as to improve the therapy work.

In view of the above-mentioned situation, an object of the first embodiment of the present invention is to provide a muon monitoring system for particle radiation therapy capable to measure, in position selectively and in time selectively, delay positrons emitted from a human body due to irradiation with charged particle radiation pulses, whereby μSR signals of positive muons stopped at the Bragg peak position of the charged particle radiation pulses are obtained to exactly know the radiation therapy effects.

Further, an object of the second embodiment is to provide a muon monitoring system for particle radiation therapy, wherein while the depth of the Bragg peak can be freely controlled so that the system can be freely applied to particle radiation therapy of any depth, capable to measure, in position selectively and in time selectively, delay positrons emitted from a human body due to irradiation with charged particle radiation pulses, whereby μSR signals of positive muons stopped at the Bragg peak position of the charged particle radiation pulses are obtained to exactly know the radiation therapy effects.

Still further, an object of the third embodiment is to provide a muon monitoring system for particle radiation therapy, wherein while the position of the Bragg peak can be freely controlled to the left or to the right so that the system can be applied to particle radiation therapy where the therapeutic objective part extends to the right and left, capable to measure, in position selectively and in time selectively, delay positrons emitted from a human body due to irradiation with charged particle radiation pulses, whereby μSR signals of positive muons stopped at the Bragg peak position of the charged particle radiation pulses are obtained to exactly know the particle radiation effects.

Means to Solve the Invention

To attain the above-described objects, in the first embodiment, a muon monitoring system for particle radiation therapy, for performing a particle radiation therapy by irradiating a human body with high energy charged particle radiation accelerated by an accelerator, is characterized in that the system includes a shield, arranged to correspond to a Bragg peak position of high energy particle radiation pulses irradiated to a human body, and selectively passing, among particle and radiation produced due to the high energy particle radiation pulses, delay positrons emitted due to decay of muons stopped at a position corresponding to the Bragg peak position; a positron detector containing a multiple positron counters for detecting the positrons from a designated direction, arranged to correspond to the Bragg peak position, detecting the delay positrons passing through the shield for each of the positron counters; and a control/analysis apparatus generating a delay signal with a predetermined width at a timing delayed by a predetermined time period from a completion of the radiation of the high energy particle radiation pulses, operating the positron detector while generating the delay signal, performing a process to detect the delay positrons, and performing a process to generate μSR signals by analyzing detected results obtained by operating the positron detector for a predetermined number of times.

Further, in the second embodiment, the muon monitoring system for particle radiation therapy according to the first embodiment is characterized in that the system additionally includes an in-front energy absorber, arranged between the accelerator and the human body, and absorbing a part of energy of the high energy particle radiation emitted from the accelerator.

Still further, in the third embodiment, the muon monitoring system for particle radiation therapy according to the first or second embodiment is characterized in that the system further includes a beam scanning capability in the left or right direction adjusting emitting position or emitting direction of the high energy particle radiation supplied from the accelerator, and letting irradiation with the human body.

Effects of the Invention

The muon monitoring system for particle radiation therapy according to the first embodiment of the invention is capable to measure, in position selectively and in time selectively, delay positrons emitted from a human body due to irradiation with charged particle radiation pulses, whereby μSR signals of positive muons stopped at the Bragg peak position of the charged particle radiation pulses are obtained to exactly know the radiation therapy effects.

Further, in the muon monitoring system for particle radiation therapy in the second embodiment, while the depth of the Bragg peak can be freely controlled so that the system can be freely applied to particle radiation therapy of any depth, the system is capable to measure, in position selectively and in time selectively, delay positrons emitted from a human body due to irradiation with charged particle radiation pulses, whereby μSR signals of positive muons stopped at the Bragg peak position of the charged particle radiation pulses are obtained to exactly know the radiation therapy effects.

Still further, in the muon monitoring system for particle radiation therapy in third embodiment, while the position of the Bragg peak can be freely controlled to the left or to the right so that the system can be applied to particle radiation therapy when the therapeutic objective part extends to the right and left, the system is capable to measure, in position selectively and in time selectively, delay positrons emitted from a human body due to irradiation with charged particle radiation pulses, whereby μSR signals of positive muons stopped at the Bragg peak position of the particle radiation pulses are obtained to exactly know the particle radiation therapy effects.

BRIEF DESCRIPTION OF THE DRAWINGS

FIG. 1 is a plane view showing a muon monitoring system for particle radiation therapy according to the first mode of the present invention, FIG. 2 is a front view of a lead shielding plate and a plastic counter telescope portion shown in FIG. 1, FIG. 3 is a time chart showing the operating timing of the muon monitoring system for particle radiation therapy shown in FIG. 1.

MODE FOR CARRYING OUT THE INVENTION

Principle Explanation of the Present Invention

Figure 4:
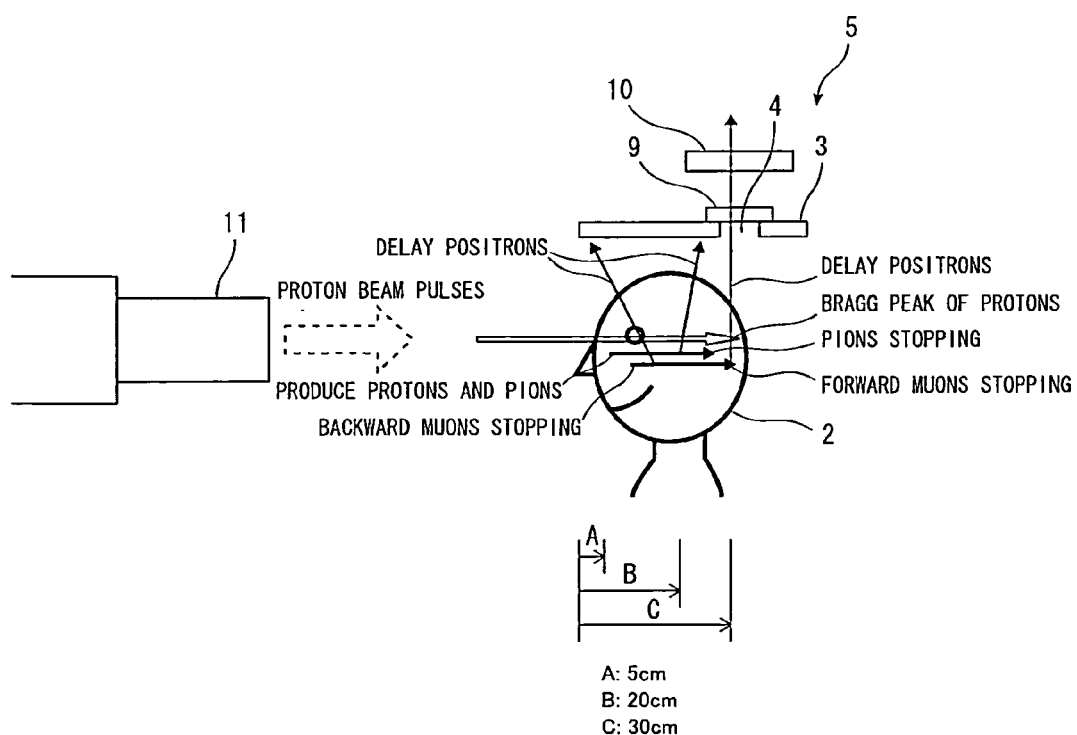
FIG. 4 is a schematic view showing an example of the operation of the muon monitoring system for particle radiation therapy shown in FIG. 1.

The principle of the present invention will be explained in advance of the detailed explanation of a muon monitoring system for particle radiation therapy according to the present invention.

First, the inventor of the present invention performed a concrete examination about the particle radiation therapy using the 230 MeV proton beams for which all related experimental data exists.

As a result, focusing on the fact that the stop position of spin-polarized positive muons which are produced concurrently by a part of proton beam pulses, and the Bragg peak position of the proton beam pulses are mostly coincide, it turned out that observation of physicochemical radiological effect of the living thing in the molecular level at the Bragg peak position can be performed when the positron (delay positron) which are produced due to decay of positive muons are measured (principle of the present invention).

Next, the contents of examination will be concretely explained about the relation between 230 MeV proton beams and positrons (delayed positrons) which are produced due to decay of positive muons.

First, 230 MeV protons make a Bragg peak at a deep position of 30 cm in a living body. In this process, positive pions of about 90 MeV are produced, and ⅓₀ of them are decayed into positive muons while flying in the substance, ⅒ of them have energy of about 100 MeV and progress in the front direction which is almost the same as that of protons, and stop at a depth of 30 cm. The muons are spin-polarized in the counter direction of a direction of movement of protons. Positive muons are decayed with a life time of 2.2 microseconds, and emit positrons having the highest energy of 50 MeV asymmetrically to the direction of the spin.

Moreover, the proton beam emitted from an accelerator has a specific pulse time structure corresponding to RF electric field characteristic for acceleration. All of the beams of high energy protons, alpha, electrons, gamma or the like, which are produced as a result of the nuclear reaction of the proton beam and biological material, are emitted with concentrated time within several ns in the vicinity of the proton beam pulses; and all the signals existing among several 100 nanoseconds to several microseconds between respective proton beam pulses become positrons (delay positrons) from the positive muons. Moreover, the positrons from the positive muons which have stopped at positions other than the Bragg peak can be removed by a lead shield having a predetermined thickness. That is, the signals other than the signals from muons which have stopped at the Bragg peak position can be easily removed by appropriately preparing the time characteristic of the measuring instrument of the positrons, and by appropriately manufacturing the shield of the positrons.

In this way, by measuring the delay positron emitted in synchronization with the proton beam pulse by selecting a time and by selecting a position, a muon spin signal at the Bragg peak position can be obtained. By this technique, not only the monitoring of the Bragg peak position of the proton can be performed, but also the physicochemical elucidation of a radiological effect of a living thing in the molecular level can be performed, so that a progress in the particle radiation therapy can be attained.

In the following, the principle of the present invention will be explained in accordance with an itemization with a practical constitution and numerical values with reference to FIGS. 7 to 12 and mathematical expressions.

Figure 8:
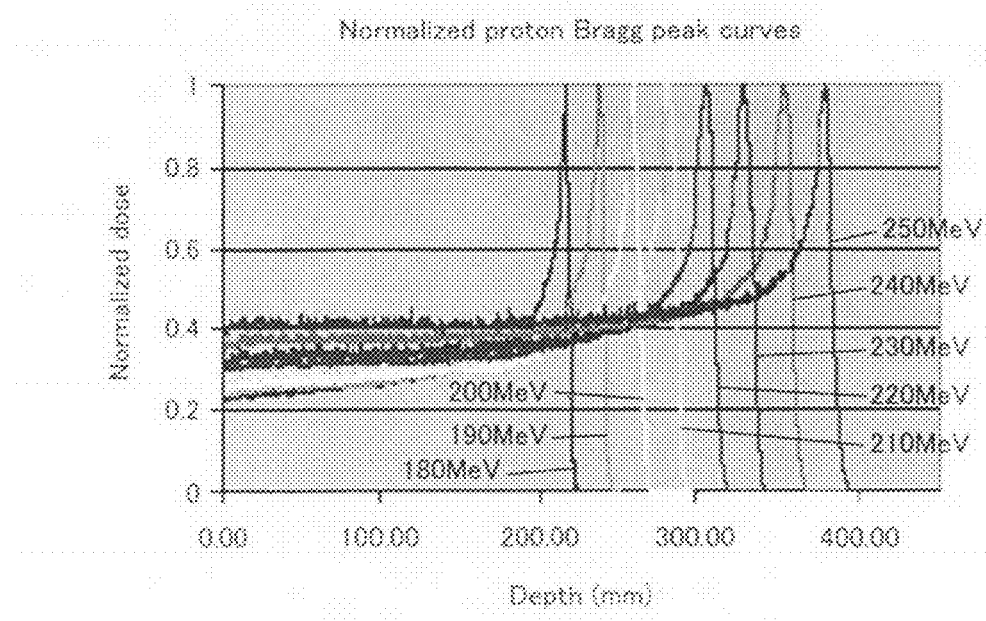
FIG. 8 is a graph showing the dependence of the radiological effect on a thickness of a living body for proton beams of various energies.

(1) FIG. 8 is a graph illustrating the dependence of the radiological effect on the thickness of the living body for the proton beams of various energies [reference 1]. As is apparent from the graph, when a living body or the like are irradiated with a proton beam of 230 MeV used for cancer therapy, a Bragg peak is generated at a deep position of 30 cm from the surface of the living body.

(2) As shown in FIG. 8, when a living body is irradiated with a 230 MeV proton, a Bragg peak is generated at a deep position of 30 cm from the surface of the living body. At this time, almost all of the positive pions, which are produced by the nuclear reaction of protons, stop at a position of a depth of 20 cm from the surface of a living body. In addition, during this process, 1/30 of the positive pions are changed to muons, and a high energy component (forward muons) stop at a position of a depth of 30 cm from the surface of a living body, and backward muons stop at position of a depth of 5 cm from the surface of a living body.

Furthermore, when the 230 MeV proton with which the living body is irradiated is 10 nano A, positive pions in the vicinity of 90 MeV shown in the following formulas are emitted in the direction of the protons.

$$N_\pi = I_P \times (d\sigma/d\Omega) \times \Delta\Omega \times n \times t \quad (1)$$
$$= (0.63 \times 10^{11}) \times (0.1 \times 10^{-27}) \times \pi/4 \times (6 \times 10^{23}/18) \times 10$$
$$= 3 \times 10^6$$

Where, $N_\pi$: intensity of a positive pion[/s]
$d\sigma/d\Omega$: differential cross section of a produced positive pion [$cm^2/sr$]
$\Delta\Omega$: solid angle of a produced positive pion [sr]
n: number of molecules per unit volume [$/(cm)^3$]
t: thickness of a proton target (cm)

Furthermore, from the positive pion in the vicinity of 90 MeV, a forward muon of 100 MeV shown in the following formula is produced.

$$N_\mu = N_\pi \times (\Delta t_{s.d.}/\gamma_\pi \tau_\pi) \times (\Delta\Omega_\mu/\Delta\omega_{decay}) \quad (2)$$
$$= (3 \times 10^6) \times (1 \text{ ns}/30 \text{ ns}) \times 1/10$$
$$= 10^4$$

Where, $N_\mu$: strength of a forward muon [/s]
$N_\mu$: strength of a positive pion [/s]
$\Delta t_{s.d.}$: time up to decelerate and stop [s]
$\gamma_\pi \tau_\pi$: life time of a pion with relativistic corrections [s]
$\Delta\Omega_\mu$: solid angle for collecting muons [sr]
$\Delta\omega$: muon ejection angle when pions and muons are decayed [sr]

Figure 9:
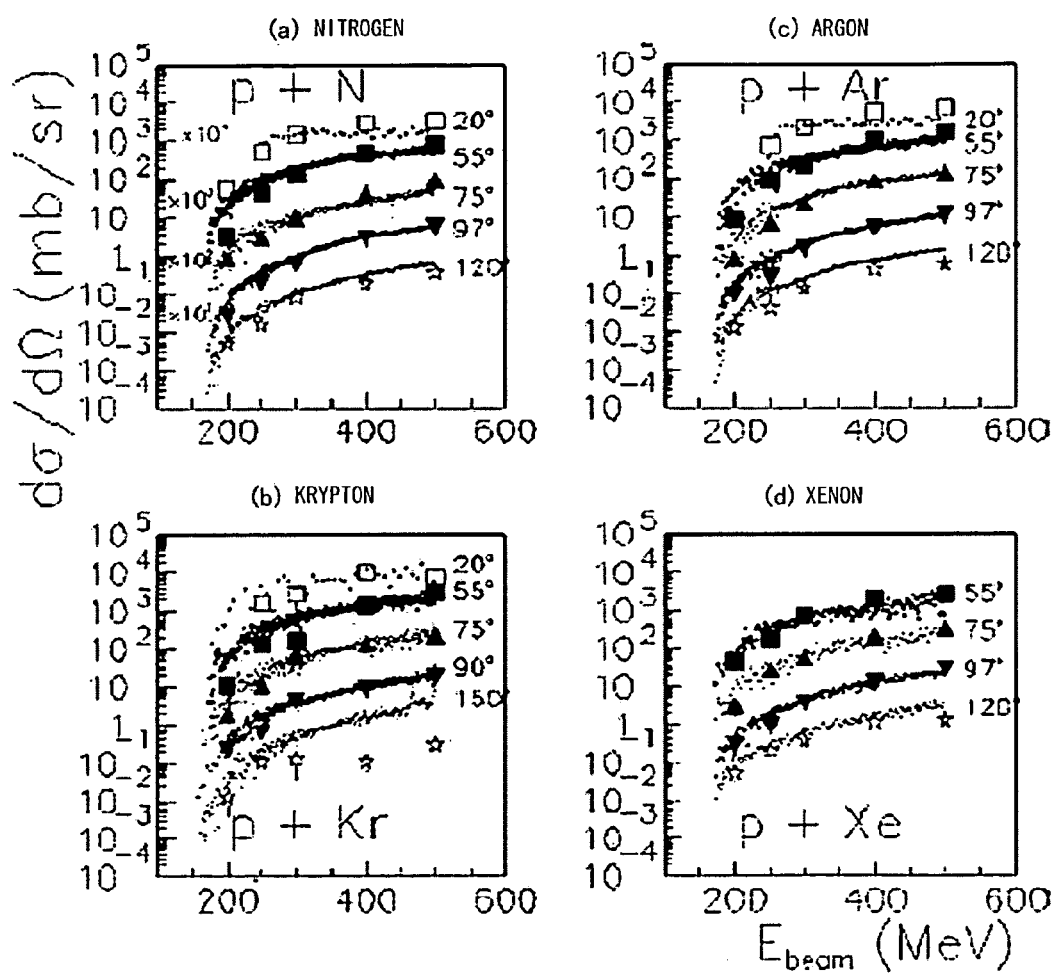
FIG. 9 is a graph showing an example of the dependence of positive pion produced differential cross sections on the proton energy, the positive pions being produced when various nuclei, such as of nitrogen, of krypton, of argon, of xenon or the like, and a proton react.

(3) In the above-mentioned evaluation, as shown in (a) to (d) of FIG. 9, when each of various nuclei, such as of nitrogen, of krypton, of argon, of xenon or the like, and a proton react, the differential cross section of a produced positive pion changes in accordance with proton energy [reference 2]. Under the present circumstances, if the energy of the pion used as the observed object is 20 degrees (11-60 MeV), even if the threshold value of the reaction between a nuclear particle and a nuclear particle such as each of various nuclei and a proton is 280 MeV or less MeV, the differential cross section of the produced positive pion has a sufficient value. And if the atom is the living body atom C (carbon), N (nitrogen), and O (oxygen) which constitutes the living body, the differential cross section of the produced positive pion in the vicinity of 90 MeV produced in ahead is $0.1 \times 10^{-27}$ $cm^2/sr$ for a proton of 230 MeV.

(4) Still further, as shown in the dependence of the cross section of a produced proton and pion on the proton energy [reference 2], a proton of 230 MeV reacts to a nucleus in the living body atom existing in an area from the surface of the living body to the depth of 10 cm; the positive pion in the vicinity of 90 MeV corresponding to 1/20,000 of the proton of 230 MeV is emitted in the direction of the proton; and 1/30 of it changes to positive muons, and stop at a position of 30 cm from the surface of the living body. Also, the remaining positive pions emitted in the direction of the proton stop at a position up to 20 cm from the surface of the living body, and are changed to positive muons of 4 MeV in 26 ns.

Figure 10:
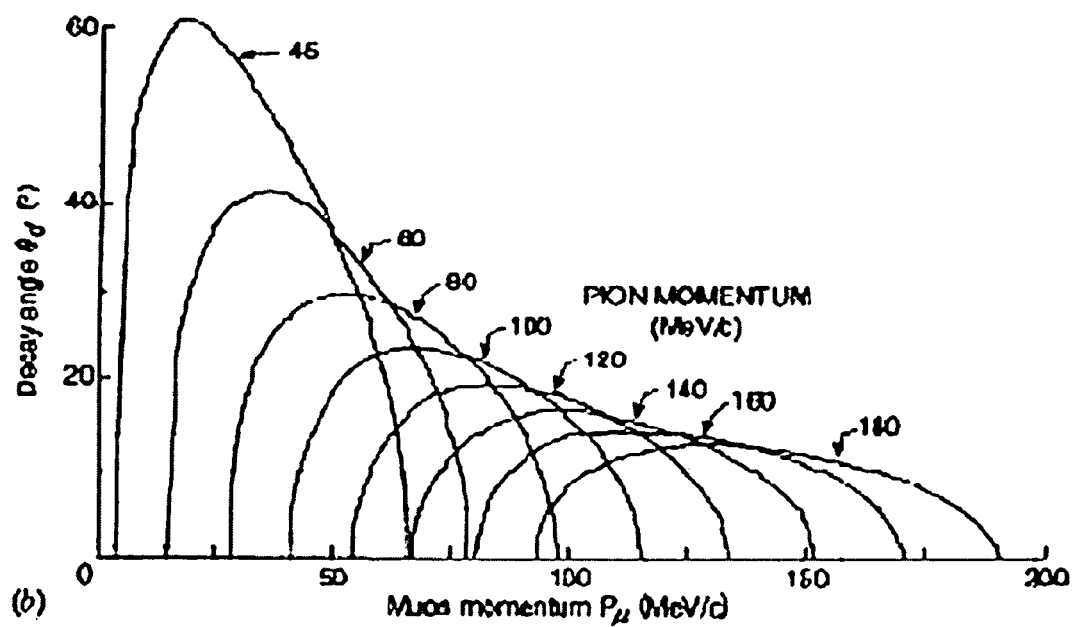
FIG. 10 is a graph showing distribution of momentum and a spread of angles of the muons which are produced to various pion momentum (energy) when pions are decayed and muons are produced.

(5) Still further, as shown in FIG. 10, as is apparent from the graph showing the relation between the momentum distribution and the spread of its angle of each muon produced at various pion momentum (energy) when each of such pions decays [reference 3]; when the pions of 176 MeV/c (85 MeV) decay, forward muons of 189 MeV/c (107 MeV) and backward muons of 90 MeV/c (31 MeV) are produced in a cylindrical geometry of 15 degrees centering on the flight path of the pions.

Still further, although the positive muons obtained by the change of the positive pions while flying are distributed from 30 MeV to 110 MeV, about 1/10 of them are 100 or more MeV, and they run in the same direction (front) as the direction of flight of the positive pions (the direction of the protons) (forward muons).

Figure 11:
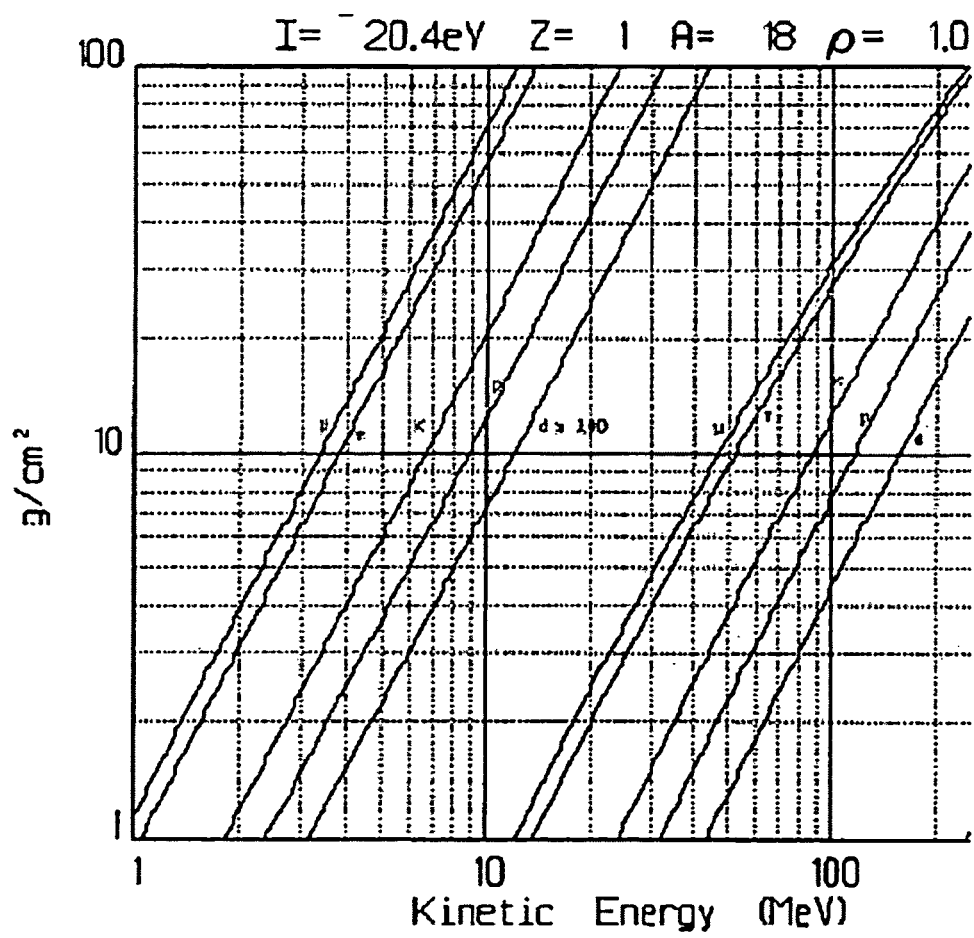
FIG. 11 is a graph showing a dependence of the range of each particle in water (flight distance until it stops) on energy.

Still further, as shown in FIG. 11, as is apparent from the graph showing the energy dependence of range of various particles in water, with a characteristic dependency on energy (reference 4), the range of the proton of 230 MeV is 30 cm, that of the pion of 90 MeV is 23 cm, that of the forward muon of 100 MeV is 30 cm, and that of the backward muon of 30 MeV is 5 cm.

(6) As is apparent from each of these experimental data, the forward muons of 100 MeV, which are produced when a living body is irradiated with the protons of 230 MeV, stop at a position of 30 cm from the surface which is the same as the Bragg peak Position of the protons.

Still further, large spin polarization of the positive muons (forward muons), which have stopped at the same position as the Bragg peak position of the protons, appears in the opposite direction to the direction of the forward movement of the protons; they decay by a time constant of 2.2 microseconds; and the high energy positrons of up to 50 MeV mostly emitted in the direction of the spin of the positive muons (counter direction of the direction of the forward movement of the proton beam) are emitted.

(7) By observing the time change of the high energy positron intensity with reference to proton beam pulse time as a time reference, the movement of the spin of the positive muons can be measured at the Bragg peak position, whereby the intensity of the magnetic field of the molecular level at that position and its change in time can be probed so that it becomes possible to observe the living-thing physical chemistry phenomenon at the Bragg peak position of the proton beam (the μSR method) [reference 3].

(8) Still further, by starting the observation of the positrons after 10 ns or more after finishing the irradiation of the proton beam pulses, background noises such as high energy alpha, protons, neutrons, gamma rays, electrons, or the like which are promptly produced by the proton beam can be removed. Still further, the delay beta ray and the gamma ray from the produced radioactive nuclei have weak intensity. Still further, with respect to the positrons which are produced when the positive muons produced by the stopped positive pions are decayed, or the positrons which are produced when the backward muons produced by the flying positive pions are decayed, since the stop positions of these muons are at an upper stream of 10 cm or more compared with the stop positions of the forward muons, by arranging appropriate lead shields having apertures only at the Bragg peak position of the proton beam as shown in FIG. 12, it is possible to pass and measure only the delay positrons emitted from the Bragg peak position of the proton beam, while the delay positrons emitted from the positions other than the Bragg peak position are completely blocked.

(9) Still further, assume that the proton beam strength is 10 nA ($0.63 \times 10^{11}$/s), then, as shown in the formula (2), the number of the positive muons which stop at the Bragg peak position of the protons and which are spin polarized is 10,000 per second. Therefore, by using a positron counter having a solid angle of 10%, about 1000 pieces per second of positrons (delay positrons) can be observed, so that a μSR signal useful for the elucidation of the living-thing physical chemistry phenomenon of a radiological effect can be obtained by about 30 seconds after starting the irradiation of the proton beam pulses.

(10) Still further, the positions of the positron production can be determined within 5 mm by employing a finely segmented plastic counter telescope or the like realized by more than two position sensitive positron counter boards made of finely segmented in the x-y directions in the shapes of cells. It can be used as a monitor of the position of the Bragg peak because of correlation between the Bragg peak positions of the protons and the stop positions of forward muons.

Figure 12:
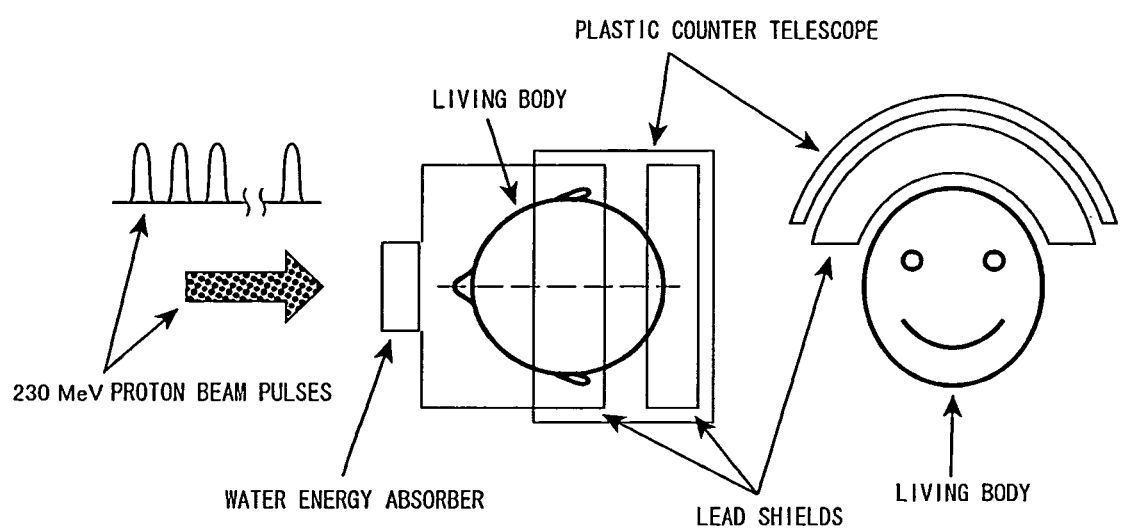
FIG. 12 is a schematic configuration diagram showing a basic configuration example of a muon monitoring system for particle radiation therapy according to the present invention.

(11) The above quantitative explanation has been provided for the case of the proton energy of 230 MeV with the Bragg peak position of 30 cm, however, for a change in the depth direction of the Bragg peak of the proton beam, it is sufficient to place water having a thickness corresponding to the difference from 30 cm as shown in FIG. 12. By the change of the proton beam and the living body on the beam vertical plane, it is possible to correspond to the change of the positions in the depth and the vertical plane.

REFERENCES

[1] Bragg peak pdf Ebook Download; Abstract11D:8159
[2] J. Matensson et al. Phys. Rev. C62 (2000)014610.
[3] K. Nagamine, Introductory Muon Science, Cambrige Univ. Press, 2003, pp. 1-208.
[4] TRIUMF Kinemmatic-Handbook-P3 (1987).
[5] K. Nagamine et al. Chem. Phys. Lett 87 (1982)186.
[6] K. Nagamine et al. Proc. Japanese Academy, Ser. B83 (2007)120-126.
[7] K. Nagamine et al. Physica B404 (2009)1020-1023.

<<The 1st Mode>>

FIG. 1 is a plane view showing the 1st mode of the muon monitoring system for particle radiation therapy using the above-described principle according to the present invention.

The muon monitoring system 1a for particle radiation therapy shown in this figure is comprised of: a plastic counter telescope 5 arranged in the position corresponding to an opening 4 of lead shields 3 arranged to cover portions other than the range corresponding to a therapeutic part (Bragg peak position) of a patient (human body) 2 to accept therapy, and measure the delay positrons emitted outside from the opening 4 of the lead shields 3; a console 6 arranged in an operating room or the like adjacent to a particle radiation therapy room provided with these lead shields 3 and a plastic counter telescope 5, and operated by a doctor or the like; a control/analysis apparatus 7 arranged in the operating room or the like for analyzing the measurement results output from the plastic counter telescope 5 based on the contents of the operation of the console 6, a pulse signal output from an accelerator (illustration is omitted), or the like, to calculate μSR signals and the produced positions of delay positrons; and a display apparatus 8 arranged adjacent to the console 6 for displaying images of the contents of the operation of the console 6, the analyzed results obtained by the control/analysis apparatus 7, or the like. At each time when a patient (human body 2) to accept therapy is irradiated with proton beam pulses of 230 MeV emitted from the accelerator, only the delay positrons produced at the Bragg peak position are selected in terms of position and time. Then, after continuously measuring the delay positrons for a predetermined time period, the measured results are analyzed, and the μSR signals and the produced positions of the delay positrons are displayed on the display apparatus 8.

The lead shields 3 are configured of lead plates each having a predetermined thicknesses, with an opening 4 formed on a location corresponding to the Bragg peak position (therapeutic part) generated in the human body. The lead shields 3 shield, among respective particles and respective radiations produced by the reactions of 230 MeV proton beam pulses emitted from the accelerator with nuclei of atoms configuring the human body, the delay positrons or the like produced at positions other than the Bragg peak position. And by the opening 4, only the delay positrons produced at the Bragg peak position are passed, and are entered into the plastic counter telescope 5.

The plastic counter telescope 5 is, as shown in FIG. 2, configured of two position sensitive positron counter boards having a plurality of plastic counters (positron counters) segmentalized in the shapes of cells in such a way that the positions of the produced positrons can be determined within 5 mm. The first position sensitive positron counter board 9 is arranged on the outside of the lead shields 3 so as to correspond to the opening 4 of the lead shields 3, and the second position sensitive positron counter board 10 is arranged outside and apart from the first position sensitive positron counter board 9 by a predetermined distance in such a way that the passages of the positrons and the produced positions of the delay positrons can be calculated by the simultaneous counting by the first position sensitive positron counter board 9 and the second position sensitive positron counter board 10. And, during a period from a time when a count start instruction is supplied from the control/analysis apparatus 7 to a time when a count end instruction is supplied, the delay positrons from the direction determined by the passing positions of each of the positron counters of the first position sensitive positron counter board 9 and the passing positions of each of the positron counters of the second position sensitive positron counter board 10 (the delay positrons passed through the opening 4 of the lead shields 3) are counted, and the calculated results of positron produced positions and times of delay simultaneous signals are supplied to the control/analysis apparatus 7.

Still further, the console 6 is arranged in the operating room or the like adjacent to the particle radiation therapy room, and when various manual operation buttons or the like are operated by a doctor or the like, the console 6 generates instruction signals according to the contents of the operation, and supplies them to the control/analysis apparatus 7.

The control/analysis apparatus 7 is arranged in the operating room or the like and performs the following processes: a process to generate an irradiation start signal and to supply it to the control apparatus of the accelerator when an irradiation start instruction is delivered from the console 6; a process to generate an irradiation end signal and to supply it to the control apparatus of the accelerator when an irradiation end instruction is delivered from the console 6; a process to generate, at each time when a synchronization signal representing that proton beam pulses of 230 MeV is being emitted from the control apparatus of the accelerator side in a state where an analysis permission instruction is supplied from the console 6, a delay signal having a predetermined width (for example, a width of 100 nanoseconds to several microseconds) by a delay of 10 ns from the falling time of the synchronization signal; a process to supply a count start instruction to the plastic counter telescope 5 in synchronization with the rise of the delay signal, to start to count the delay positrons by each positron counter of the first position sensitive positron counter board 9 and by each positron counter of the second position sensitive positron counter board 10, and to accumulate information of the positron produced positions and the times of the delayed simultaneous signals from the simultaneous measurements of the first position sensitive positron counter board 9 and the second position sensitive positron counter board 10; a process to supply a count end instruction to the plastic counter telescope 5 in synchronization with the fall of the delay signal, and to stop the counting operation of each positron counter; a process to accommodate the counted result by each positron counter and to store it; a process to analyze the counted result from each storing positron counter when a predetermined time of, for example, 30 seconds, from the first output of the synchronization signal from the control apparatus of the accelerator side (a time period sufficient for the count value of each positron counter to generate the μSR signal) has passed, to generate the μSR signals, and to calculate the produced positions of the delay positrons (positron produced positions); a process to obtain the μSR signal sectionalized for each positron produced position; or the like.

Still further, the display apparatus 8 is arranged to be adjacent to the console, and displays the contents of operation of the console, the analysis results of control/analysis apparatus, or the like.

Next, the operation of the muon monitoring system 1a for particle radiation therapy is explained with reference to the plan view shown in FIG. 1, and the front view shown in FIG. 2.

First, by a nurse, a doctor, or the like, a patient (human body 2) to be a therapeutic objective is placed on a therapy table installed in the particle radiation therapy room, and then the lead shields 3 formed to have a shape corresponding to a therapeutic objective part and the plastic counter telescope 5 are attached and fixed to the therapeutic objective part of the patient (human body 2).

Then, after the position of the therapy table is adjusted by the nurse, the doctor, or the like so that the therapeutic objective part is placed to a position corresponding to an irradiation apparatus 11 linked to an emitting path of the accelerator, persons other than the patient come out from the particle radiation therapy room, and the door of the particle radiation therapy room is closed.

After safety is checked by the nurse, the doctor, or the like, preparation of particle radiation therapy is completed.

Then, when the console 6 is operated by the doctor in the operating room to input an irradiation start instruction, an irradiation start signal is generated by the control/analysis apparatus 7 is supplied to the control apparatus of the accelerator.

By this means, the proton generation source, the linear accelerator, the ring accelerator, or the like is started to work by the control apparatus of the accelerator, so that the protons obtained by the proton generation source are introduced into the linear accelerator, and they are accelerated to have a predetermined energy, then, they are introduced into the ring accelerator, and they are accelerated until they have 230 MeV.

And, when the protons are accelerated up to have 230 MeV, an emitting path, abeam transport system, the irradiation apparatus 11, or the like is started to work by the ring accelerator, so that the protons accelerated up to have 230 MeV are introduced to the irradiation apparatus 11 installed in the particle radiation therapy room through a path from the ring accelerator, emitting path, beam transport system, and irradiation apparatus 11, and the therapeutic objective part of the patient (human body 2) is irradiated with the proton beam pulses each having a several ns width, and the synchronization signal indicating that the proton beam pulses have been emitted is generated by the control apparatus of the accelerator and is supplied to the control/analysis apparatus 7.

Still further, in parallel to the above-described operation, the proton beam pulses with which the patient (human body 2) was irradiated reach the therapeutic objective part (it is a depth of 30 cm in the living body) of the patient (human body 2); a Bragg peak is generated; a part of proton beam pulses becomes positive pions of about 90 MeV in the human body 2; the 1/30 of them are decayed to become positive muons while flying the inside of the human body 2; the 1/10 of them have the energy of about 100 MeV and become positive muons with spin polarization in the direction of movement and progress in the almost same direction as the proton beam pulses; and stop at the therapeutic objective part (it is a depth of 30 cm in the living body) of the patient (human body 2).

And when the average lifetime of 2.2 microseconds has passed, the positive muons (forward muons) stopped at the therapeutic objective part (it is a depth of 30 cm in the living body) of the patient (human body 2) are decayed, and the positrons having the maximum energy of 50 MeV are emitted anisotropically to the direction of the spin.

Still further, as shown in (a) and (b) of FIG. 3, in parallel to the above-described operation, each time when the synchronization signal showing that the proton beam pulses are emitted falls, the control/analysis apparatus 7 detects the fact, and as shown in (c) of FIG. 3, when 10 ns has passed after each fall of the synchronization signal, it starts to generate a delay signal, and the count start instruction is supplied to the plastic counter telescope 5 in synchronization with the rise of the delay signal, so that, by each positron counter of the first position sensitive positron counter board 9 and each positron counter of the second position sensitive positron counter board 10, counting of the delay positrons (delay positrons emitted due to the decay of the forward muons) is started.

On this occasion, even if background noises are produced such as particles or radiation other than the delay positrons produced at the Bragg peak position by the reactions of 230 MeV proton beam pulses emitted from the accelerator with nuclei of atoms configuring the human body, such as, for example, high energy alpha, protons, neutrons, gamma rays, electrons, or the like, when the delay signal rises after 10 ns has passed from the fall of the synchronization signal, most of the background noises disappear so that the background noises are shielded in terms of time.

Still further, as shown in FIG. 4, since the delay positrons produced when the backward muons decay, the delay positrons produced when the muons which have stopped at the upstream side from the Bragg peak position decay, or the like, are shielded in the three-dimensional space by the lead shields 3, only the delay positrons produced at the Bragg peak position pass through the opening 4 of the lead shields 3 to enter into each positron counter of the first position sensitive positron counter board 9, and each positron counter of the second position sensitive positron counter board 10, and are counted.

After this, when 100 nanoseconds to several microseconds have passed since the rise of the delay signal, the control/analysis apparatus 7 detects the fact, stops the generation of the delay signal, supplies, in synchronization with the fall of the delay signal, the count end instruction to the plastic counter telescope 5 to stop the counting operation of each positron counter of the first position sensitive positron counter board 9 and each positron counter of the second position sensitive positron counter board 10, and takes in and memorizes the counted result, as information on the produced positions of the positions and the times of the delay simultaneous signals, obtained by each positron counter of the first position sensitive positron counter board 9 and each positron counter of the second position sensitive positron counter board 10.

After this, each time when the therapeutic objective part of the patient (human body 2) is irradiated with the protons accelerated to 230 MeV as the proton beam pulses, the control/analysis apparatus 7 repeats a count start operation and count end operation of the above-mentioned each positron counter of the first position sensitive positron counter board 9 and each positron counter of the second position sensitive positron counter board 10, to store the counted values of the delay positrons emitted due to the decay of the forward muons.

Then, by making the time when the first synchronization signal is output from the control apparatus of the accelerator side as a reference, when a predetermined time period of, for example, 30 seconds (up to a time when the count values of each positron counter of the first position sensitive positron counter board 9 and each positron counter of the second position sensitive positron counter board 10 become values sufficient to generate the μSR signals) has passed, the control/analysis apparatus 7 starts to analyze the stored counted results of each positron counter of the first position sensitive positron counter board 9 and each positron counter of the second position sensitive positron counter board 10, generates the μSR signals, calculates the produced positions of the delay positrons, and displays images of the μSR signals, segmented for each of the produced positions of the positrons, on the display apparatus 8.

As such, when the human body 2 is irradiated with the proton beam pulses, a part of the proton beam pulses change to the positive pions, and further, a part of them change to the positive muons and stop at the Bragg position, and after that they decay with the time constant of 2.2 microseconds to emit the delay positrons. According to the first mode, since the μSR signals and the Bragg peak position information are generated by measuring the delay positrons, the effects as described below can be obtained (effects of the first embodiment).

(a) First, it can carry out immediately with the existing proton radiation therapy institution. In this case, although using a fast extraction proton synchrotron is ideal, a synchrotron or a cyclotron with time structure can also be used. Moreover, it is applicable also to an institution of a heavy ion beam.

(b) Moreover, the observation under particle radiation therapy is possible on site and in time, as well as data acquisition with spatial resolution of less than 5 mm and within less than 30 seconds can be made possible.

(c) Moreover, not only the position monitoring of the Bragg peak of a positron but also the elucidation of a radiological effect in the living-thing physical chemistry phenomenon at the molecular level can be made possible, so that the particle radiation therapy can be progressed. Also, as examples of the target phenomena, there are (1) determination of underwater radical formation density and thereby the determination of the proton Bragg peak position, (2) observation of a magnetic change of hem protein, and (3) observation of change of the electron transport in protein and DNA.

(d) With the use of a multiple position sensitive positron detector such as the plastic counter telescope 5, the passage of a positron can be selected so that the spatial of a generating source of the μSR signals can be raised.

(e) Beyond the beam diagnosis, the essence of the radiological effect in the living-thing physical chemistry phenomenon by a particle radiation and cancer therapy are able to be revealed.

<<The 2nd Mode>>

Figure 5:
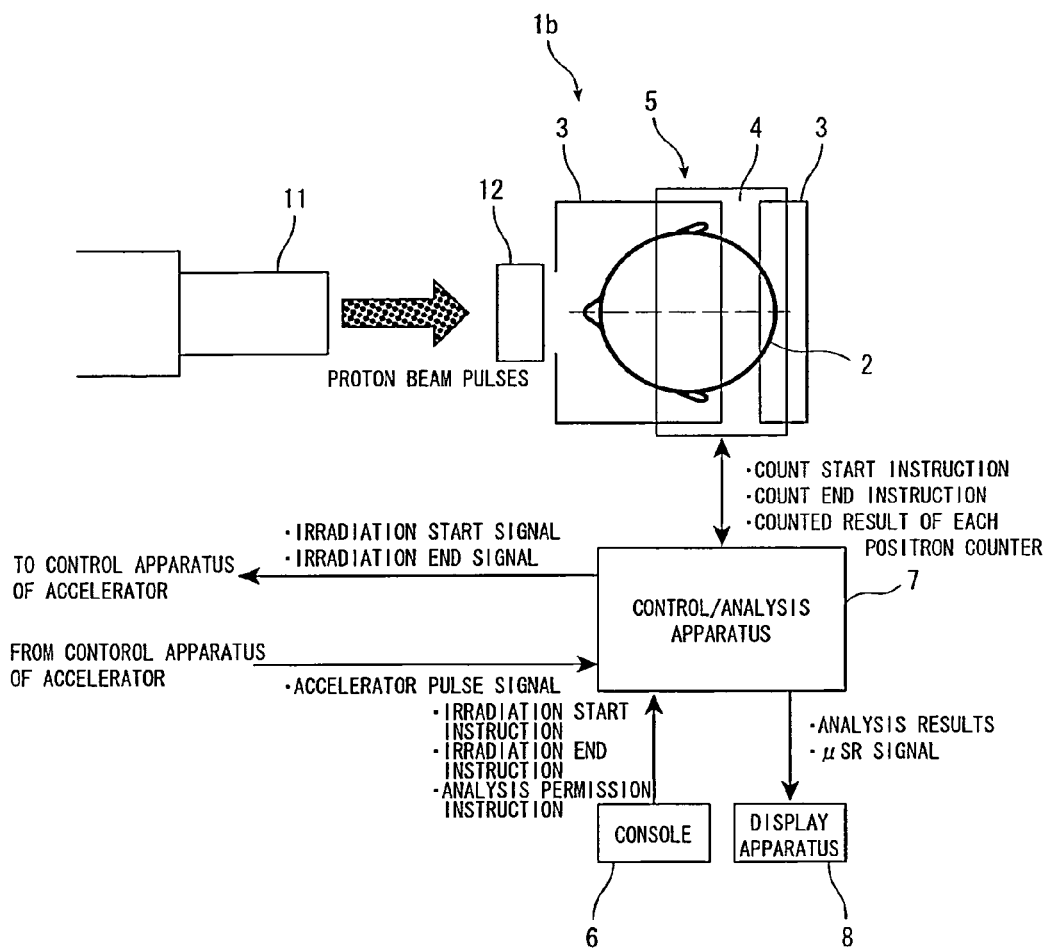
FIG. 5 is a plane view showing a muon monitoring system for particle radiation therapy according to the second mode of the present invention.

FIG. 5 is a plane view showing a muon monitoring system for particle radiation therapy according to the second mode of the present invention. Note that, in this figure, each of the same parts as in FIG. 1 is denoted by the same symbol.

The difference between the muon monitoring system 1a for particle radiation therapy shown in FIG. 1 and the muon monitoring system 1b for particle radiation therapy shown in this figure is that an in-front energy absorber 12 is arranged between the proton beam pulse entrance of the irradiation apparatus 11 and a patient (human body 2), so that, when protons accelerated to 230 MeV are led to the irradiation apparatus 11 installed in the particle radiation therapy room, and the therapeutic objective part of the patient (human body 2) placed on the therapy table are irradiated with the protons as a proton beam pulse having a width of several ns, a Bragg peak is generated at a position shallower than the depth of 30 cm in the living thing.

The in-front energy absorber 12 is constructed to be able to freely adjust its thickness and is constructed by a water tank filled with water inside thereof, or a laminated water tanks each having a predetermined thickness and being filled with water inside thereof, so as to absorb a part of the energy of the proton beam pulse emitted from the proton beam pulse entrance of the irradiation apparatus 11, and to generate the Bragg peak at a position shallower than the depth of 30 cm in the living thing.

As such, according to the second mode, the in-front energy absorber 12 is arranged between the proton beam pulse entrance of the irradiation apparatus 11 and the patient (human body 2), so that, when protons accelerated to 230 MeV are led to the irradiation apparatus 11 installed in the radiation therapy room, and the therapeutic objective part of the patient (human body 2) placed on the therapy table are irradiated with the protons as a proton beam pulse having a width of several ns, a Bragg peak is generated at a position shallower than the depth of 30 cm in the living thing, so that particle radiation therapy can be made to perform in the therapeutic part of any depth of the human body 2 (effect of the second embodiment).

<<The 3rd Mode>>

Figure 6:
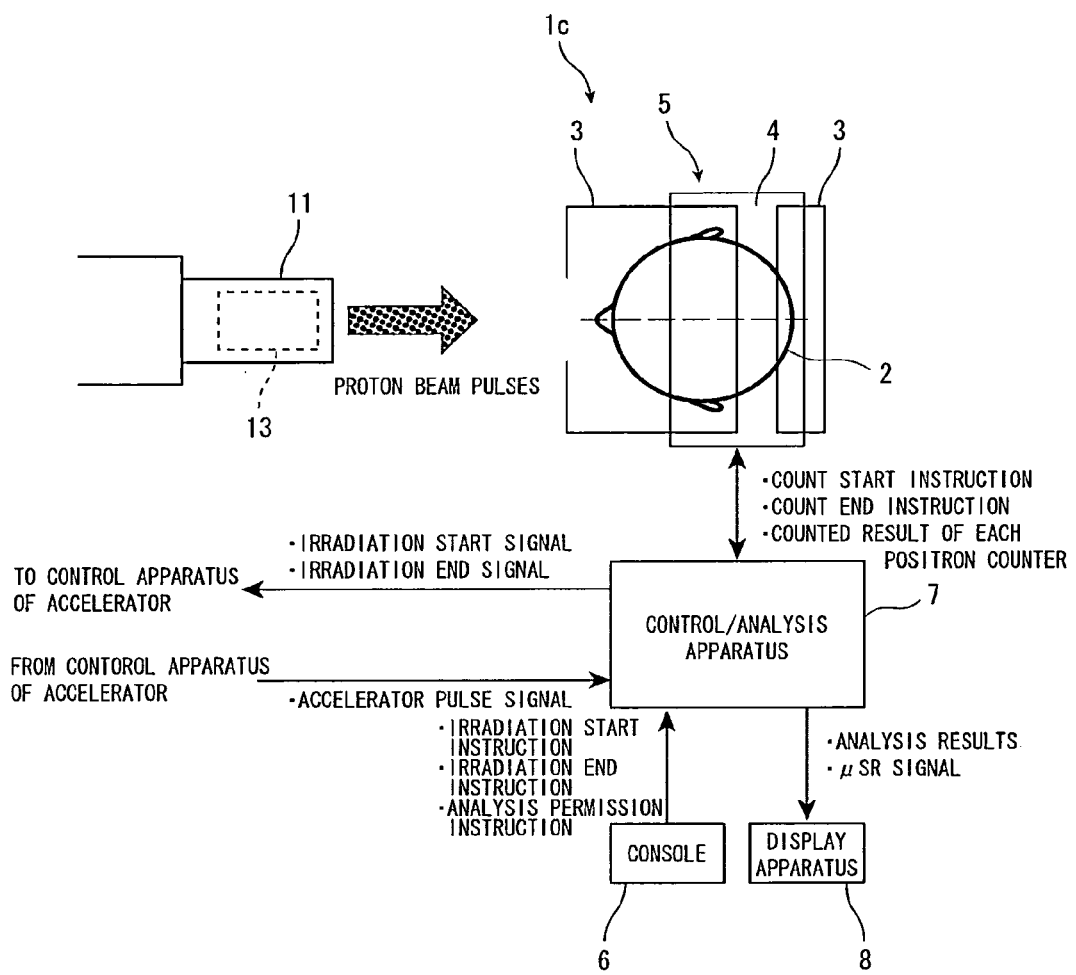
FIG. 6 is a plane view showing a muon monitoring system for particle radiation therapy according to the third mode of the present invention.
Figure 7:
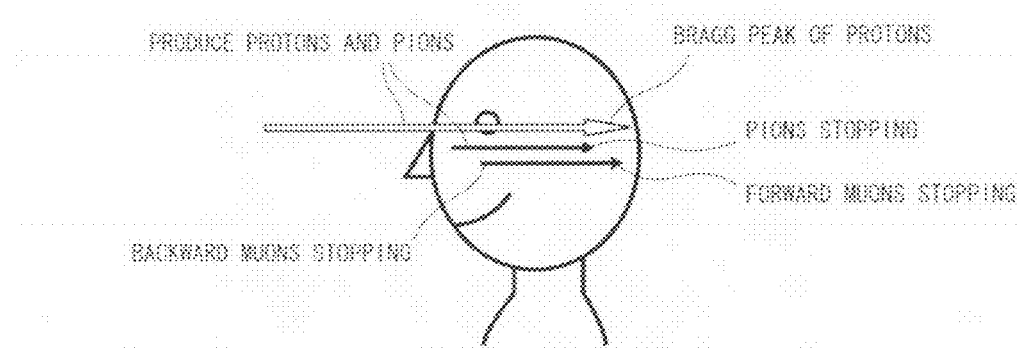
FIG. 7 is a schematic view showing the Bragg peak position of a proton in a living body, a stop position of a positive pion, a stop position of a forward muon, and a stop position of a backward muon.

FIG. 6 is a plane view showing a muon monitoring system for particle radiation therapy according to the third mode of the present invention. Note that, in this figure, each of the same parts as in FIG. 1 is denoted by the same symbol.

The difference between the muon monitoring system 1a for particle radiation therapy shown in FIG. 1 and the muon monitoring system 1c for particle radiation therapy shown in this figure is that a beam scanner 13 scanning in the left or right direction is arranged in the irradiation apparatus 11 so as to enable to adjust the outgoing radiation direction or outgoing radiation position of the proton beam pulse emitted from the irradiation apparatus 11 and so this system can cope with a case even when the therapeutic objective part of the patient (human body 2) is large.

The beam scanner 13 scanning in the right or left direction is constructed by a multiple electromagnets or the like, so that, by operating each electromagnetic or the like in accordance with an instruction from the control/analysis apparatus 7, the outgoing radiation direction or the outgoing radiation position of the proton beam pulse emitted from the proton beam pulse entrance is moved to the right or the left.

As such, according to the third mode, the beam scanner 13 scanning in the left or right direction is arranged in the irradiation apparatus 11, the outgoing radiation direction or outgoing radiation position of the proton beam pulse emitted from the irradiation apparatus 11 connected to the ring of the accelerator is adjusted, even when the therapeutic objective part of the patient (human body 2) is large, this system is able to cope with the case, therefore, even when the therapeutic objective part spreads right and left, the particle radiation therapy can be continuously performed (effect of the third embodiment).

INDUSTRIAL APPLICABILITY

The present invention relates to a muon monitoring system for particle radiation therapy used in radiology or the like, and in particular, relates to a muon monitoring system, for particle radiation therapy, enabling direct detection of the radiological effect at a Bragg peak, and therefore, has an industrial applicability.

| EXPLANATION OF SYMBOLS | |
|---|---|
| 1a, 1b, 1c: | muon monitoring system for particle radiation therapy |
| 2: | human body |
| 3: | lead shields (shields) |
| 4: | opening |
| 5: | plastic counter telescope (positron detector) |
| 6: | console |
| 7: | control/analysis apparatus |
| 8: | display apparatus |
| 9: | first position sensitive positron counter board (positron detecting plate) |
| 10: | second position sensitive positron counter board (positron detecting plate) |
| 11: | irradiation apparatus |
| 12: | head energy absorber |
| 13: | beam scanner scanning in the left or right direction |

What is claimed is:

1. A muon monitoring system for particle radiation therapy for performing a particle radiation therapy by irradiating a human body with high energy charged particle radiation accelerated by an accelerator, the system comprising:
a shield, arranged to correspond to a Bragg peak position of high energy particle radiation pulses irradiated to a human body, and selectively passing, among particles and radiation produced due to the high energy particles and radiation pulses, delay positrons emitted due to decay of muons stopped at a position corresponding to the Bragg peak position,
a positron detector including a plurality of positron detecting plates for detecting positrons from a designated direction, arranged to correspond to the Bragg peak position, detecting the delay positrons passed through the shield for each of the positron detecting plates and providing information of positron produced positions and time of delay simultaneous signals; and
a control/analysis apparatus generating a delay signal with a predetermined width at a timing delayed by a predetermined time period from a completion of irradiation of the high energy particle radiation pulses, operating the positron detector while generating the delay signal, performing a process to detect the delay positrons, and performing a process to generate μSR signals segmented for each positron generating position by analyzing detected results obtained by operating the positron detector for a predetermined number of times.

2. The muon monitoring system for particle radiation therapy as claimed in claim 1, further comprising:
an in-front energy absorber, arranged between the accelerator and the human body, and absorbing a part of energy of the high energy particle radiation emitted from the accelerator.

3. The muon monitoring system for particle radiation therapy as claimed in claim 2, further comprising:
a beam scanner scanning in the left or right direction adjusting emitting position or emitting direction of the high energy particle radiation supplied from the accelerator, and letting irradiation with the human body.

4. The muon monitoring system for particle radiation therapy as claimed in claim 1, further comprising:
a beam scanner scanning in the left or right direction adjusting emitting position or emitting direction of the high energy particle radiation supplied from the accelerator, and letting irradiation with the human body.

* * * * *